(12) United States Patent
Hazen et al.

(10) Patent No.: US 10,786,479 B2
(45) Date of Patent: Sep. 29, 2020

(54) METHODS FOR INHIBITING CONVERSION OF CARNITINE TO TRIMETHYLAMINE (TMA)

(71) Applicants: The Procter & Gamble Company, Cincinnati, OH (US); The Cleveland Clinic Foundation, Cleveland, OH (US)

(72) Inventors: Stanley Leon Hazen, Pepper Pike, OH (US); Jose Carlos Garcia-Garcia, Cincinnati, OH (US); George Franklin Gerberick, Cincinnati, OH (US); John August Wos, Mason, OH (US); David Thomas Stanton, Hamilton, OH (US); Thomas Alfred Inglin, Loveland, OH (US); Michael Reilly, Lebanon, OH (US); Angela Jane Deutsch, West Chester, OH (US); Jodie Michele Reed, Loveland, OH (US); David Blair Cody, West Harrison, IN (US)

(73) Assignees: The Procter & Gamble Company, Cincinnati, OH (US); The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 15/366,877

(22) Filed: Dec. 1, 2016

(65) Prior Publication Data

US 2017/0151250 A1    Jun. 1, 2017

Related U.S. Application Data

(60) Provisional application No. 62/261,645, filed on Dec. 1, 2015, provisional application No. 62/261,662, filed on Dec. 1, 2015, provisional application No. 62/356,422, filed on Jun. 29, 2016.

(51) Int. Cl.

| | | |
|---|---|---|
| *A61K 31/26* | (2006.01) | |
| *A61K 31/166* | (2006.01) | |
| *A61K 31/216* | (2006.01) | |
| *A61K 31/22* | (2006.01) | |
| *A61K 31/325* | (2006.01) | |
| *A61K 31/351* | (2006.01) | |
| *A61K 45/06* | (2006.01) | |
| *C07D 213/04* | (2006.01) | |
| *C07D 295/13* | (2006.01) | |

(52) U.S. Cl.
CPC ............ *A61K 31/26* (2013.01); *A61K 31/166* (2013.01); *A61K 31/216* (2013.01); *A61K 31/22* (2013.01); *A61K 31/325* (2013.01); *A61K 31/351* (2013.01); *A61K 45/06* (2013.01); *C07D 213/04* (2013.01); *C07D 295/13* (2013.01)

(58) Field of Classification Search
CPC ................... A61K 31/26; A61K 31/04

USPC ....................................................... 514/238.5
See application file for complete search history.

(56) References Cited

U.S. PATENT DOCUMENTS

| | | | |
|---|---|---|---|
| 4,335,141 A | 6/1982 | Grier et al. | |
| 4,874,788 A | 10/1989 | Smith et al. | |
| 5,547,677 A | 8/1996 | Wright | |
| 6,576,684 B1 | 6/2003 | Desobry et al. | |
| 10,550,108 B2 | 2/2020 | Tulin | |
| 2007/0199890 A1 | 8/2007 | Trogolo | |
| 2012/0157397 A1 | 6/2012 | Hazen et al. | |
| 2012/0225020 A1 | 9/2012 | Chekmenev | |
| 2013/0345171 A1 | 12/2013 | Hazen et al. | |
| 2014/0271923 A1 | 9/2014 | Reid | |
| 2016/0101062 A1 | 4/2016 | Hazen et al. | |
| 2017/0151208 A1 | 6/2017 | Hazen et al. | |
| 2018/0000754 A1 | 1/2018 | Hazen | |

FOREIGN PATENT DOCUMENTS

| | | |
|---|---|---|
| JP | 200445869 | 12/2004 |
| JP | 2006045121 A | 2/2006 |
| JP | 4099012 B2 | 6/2008 |
| WO | WO2000011041 A1 | 3/2000 |
| WO | WO0216366A1 A1 | 2/2002 |
| WO | WO2008082692 A2 | 7/2008 |
| WO | WO2010084661 A1 | 7/2010 |
| WO | WO2010138899 A2 | 12/2010 |
| WO | WO2010140902 A1 | 12/2010 |

(Continued)

OTHER PUBLICATIONS

Uda and Shitara, "Effects of benzyl isothiocyanate . . . ", Worldwide Research Efforts in the Fighting against Microbial Pathogens (2013), pp. 150-153 (see webpage below). (Year: 2013).*

(Continued)

*Primary Examiner* — Craig D Ricci
*Assistant Examiner* — Janet L. Coppins
(74) *Attorney, Agent, or Firm* — James E Oehlenschlager

(57) ABSTRACT

The invention provides a method of inhibiting the conversion of carnitine to trimethylamine (TMA) and lowering TMAO in an individual comprising administering to the individual one or more compositions comprising a compound set forth in Formula (I):

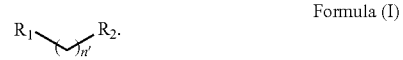

Formula (I)

Wherein the compound is administered in an amount effective to inhibit conversion of carnitine to TMA in the individual.

7 Claims, No Drawings
Specification includes a Sequence Listing.

(56) References Cited

FOREIGN PATENT DOCUMENTS

| WO | WO2013082071 A1 | 6/2013 |
| WO | WO2013188417 A3 | 3/2014 |

OTHER PUBLICATIONS https://books.google.conn/books?id=C-WVBAAAQBAJ&lpg=PA150&ots=5CF0Q0mVNm&dq=administer%20isothiocyanate%20to%20human%20bacteria&pg=PA150#v=onepage&q=administer%20isothiocyanate%20to%20human%20bacteria&f=true (Year: 2013).*

Uda and Shitara, "Effects of benzyl isothiocyanate . . . ", Worldwide Research Efforts in the Fighting against Microbial Pathogens 2013), pp. 150-153 . (Year: 2013).*

Jandhyala et al , "Role of the normal gut nnicrobiota," World Jounal of Gastroenterology (2015), pp. 8787-8803. (Year: 2015).*

Johnson et al, "Prebiotics modulate the effects of Antibiotics on Gut Microbial Diversity and functioning in vitro," Nutrients (2015), pp. 4480-4497. (Year: 2015).* http://www.anim.med.kyoto-u.ac.jp/NBR/strainsx/bw_list.aspx, webpage visited Jun. 18, 2019. (Year: 2019).*

Noriaki et al, Antimicrobial Activities of Isothiocyanate Compounds (1999), vol. 25 (1), pp. 7-13. (Year: 1999) (Year: 1999).*

Uda and Shitara, Worldwide research efforts in the fighting against Microbial Pathogens 2013, pp. 150-153. (Year: 2013).*

Borges et al. International Biodeteriation & Biodegradation 86 (2014), pp. 25-33.

http://www.compoundchem.com/2014/03/17/everyday-compounds-salicylic-acid/,Mar. 17, 2014.

International Search Report and Written Opinion, App. No. 2017/0151208, dated Feb. 10, 2017, 17 pgs.

International Search Report and Written Opinion, App. No. 2017/0151250, dated Feb. 10, 2017, 19 pgs.

International Search Report, App. No. 2018/0000754 dated Aug. 18, 2017, 13 pgs.

Jandhyala et al., "Role of the normal gut microbiota", World Journal of Gastroenterology (2015), pp. 8787-8803.

Johnson et al., "Prebiotics modulate the effects of Antibiotics on Gut Microbial Diversity and functioning in vitro", Nutrients (2015) pp. 4480-4497.

Uda and Shitara, "Effects of benzyl isothiocyanate . . . " see webpage: https://books.google.com/books?id=C-WVBAAAQBAj&pg=PA150&lpg=PA150&dq=uda+and+shitara+effects+of+benzyl+isothiocyanate&source=bl&ots=5CH4NYqPWj&sig=Ba05AKdmXhhWkOdL2J3vF2wEfwU&hl=en&sa=X&ved=2ahUKEwiXyOn_8-_fAhXom-AKHeoOCIYQ6AEwAHoECAYQAO#v=onepage&q=uda%20and%20shitara%20effects%20of%20benzyl%20isothiocyanate&f=false.

All Office Actions, U.S. Appl. No. 15/366,819.

All Office Actions, U.S. Appl. No. 15/609,791.

Aires et al,, "The antimicrobial effects of glucosinoiates and their respective enzymatic hydrolysis products on bacteria isolated from the human intestinal tract", J. Applied Microbiology, 2009; vol. 106, pp. 2086-2095.

Dufour et al., "The antibacterial properties of isothiocyanates", Microbiology (2015), vol. 161, No. 2, pp. 226-243, first published Feb. 1, 2015.

Fitzsimmons et al. "Small-Molecule Inhibition of Choline Catabolism in Pseudomonas aeruginosa and Other Aerobic Choline-Catabolizing Bacteria", Applied and Environmental Microbiology, Jul. 2011, pp. 4383-4389.

Kim et al., "Growth Inhibiting Activities of Pherrethyl Isothiocyanate and Its Derivatives against Intestinal Bacteria", Journal of Food Science (2009), vol. 74, No. 8, pp. M467-M471.

Koeth et al, "[gamma]-Butyrobetaine Is a Proatherogenic Intermediate in Gut Microbial Metabolism of L-Carnitine to TMAO", Cell Metabolism, 20, Nov. 4, 2014, pp. 799-812.

Kurepina et al. "Growth-inhibitory activity of natural and synthetic isothiocyanates against representative human microbial pathogens", Journal of Applied Microbiology (2013), vol. 115, pp. 943-954.

Vlachova et al. "Some relationships between biological activity and physicochemical properties of monosubstituted phenylisothiocyanates", Collection of Czechoslovak Chemical Communication (1966), vol. 31, No. 3, pp. 997-1008.

Weuffen et al., "Relations between chemical constitution and germicidal activity. XIV. Bacteriostatic and fungistatic properties of some aliphatic and aromatic isothiocyanates and their amine, dithiocarbamate, and thiourea analogs", pharmazie (1967), vol. 22, No. 9, pp. 506-510.

Chen et al., "Associations of gut-flora-dependent metabolite trimethylamine-N-oxide, betaine and choline with non-alcoholic fatty liver disease in adults", Scientific Reports, Jan. 2016, 6:19076-DOI:10.1038/srep19076.

Kuka et al., "Suppression of intestinal microbiota-dependent production of pro-atherogenic trimethylamine N-oxide by shifting L-carnitine microbial degradation", Life Sciences, 2014, 117, pp. 84-92.

Roberts et al. "Development of a gut microbe-targeted non-lethal therapeutic to inhibit thrombosis potential", Nature Medicine, 2018, 24-9, pp. 1407-1417.

Barfknecht et al., "Nonclassical Nicotine Antagonists", Journal of Medicinal Chemistry, 1975, 18(11), pp. 1161-1164.

Green et al., "hChaT: A tool for the chemoenzymatic generation of potential acetyl/butyrylcholinesterase inhibitors", ChemBioChem, 2009, 10(13), pp. 2191-2194.

Peterson et al., "The antagonism of nicotine-induced cardiovascular responses by DMAE and DEO analogs", European Journal of Pharmacology, 1976, 37(2), pp. 303-310.

* cited by examiner

SEQUENCE LISTING

<160> NUMBER OF SEQ ID NOS: 5

<210> SEQ ID NO 1
<211> LENGTH: 2146
<212> TYPE: DNA
<213> ORGANISM: Escherichia coli

<400> SEQUENCE: 1

| | | | | | | |
|---|---|---|---|---|---|---|
| atgagcaatc | tgagccctga | ctttgtacta | cccgaaaatt | tttgcgctaa | cccgcaagag | 60 |
| gcgtggacca | ttcctgcccg | tttttatacc | gatcagaacg | cgtttgaaca | cgaaaaagag | 120 |
| aacgtcttcg | ccaaaagctg | gatttgcgtc | gctcacagca | gcgaactggc | gaatgccaat | 180 |
| gattatgtga | cgcgtgagat | cattggcgaa | agcatcgtgc | tggtacgcgg | tcgtgataag | 240 |
| gttttgcgcg | cgttctataa | cgtgtgtccg | caccgtggtc | atcagttgtt | gagcggtgaa | 300 |
| ggaaaagcaa | aaaatgtgat | tacctgcccg | tatcacgcat | gggcattcaa | actcgatggc | 360 |
| aacctggccc | atgcacgtaa | ctgcgaaaac | gtcgccaatt | tcgatagcga | caaagcgcaa | 420 |
| ctggttccgg | tgcgtctgga | agaatatgcc | ggattcgtct | tcatcaacat | ggaccccaac | 480 |
| gccaccagcg | tagaagatca | attacccggc | ctgggcgcga | agtgctgga | agcctgcccg | 540 |
| gaagtccacg | atctgaaact | ggcggcccgc | tttaccaccc | gcacgcctgc | caactggaag | 600 |
| aacattgtcg | ataactatct | cgagtgctat | cactgtggtc | cggcgcatcc | aggtttctcc | 660 |
| gactccgtac | aggttgatcg | ttactggcac | accatgcacg | gtaactggac | gctgcaatac | 720 |
| ggtttcgcca | accgtccga | acagtcgttt | aaatttgaag | agggtacgga | tgcggcattc | 780 |
| cacggtttct | ggctgtggcc | gtgcacgatg | ctgaacgtca | ccccgatcaa | agggatgatg | 840 |
| acggtcattt | atgaattccc | ggtggattct | gaaactaccc | tgcaaaacta | cgatatttac | 900 |
| ttcaccaatg | aagagttaac | cgacgagcaa | aaatcgctga | ttgagtggta | tcgcgatgtg | 960 |
| ttccgtccgg | aagatttacg | tctggttgaa | agcgtacaga | aagggctgaa | atcgcgtggc | 1020 |
| tatcgtggtc | aggggcgcat | catggccgac | agtagcggta | gtggcatttc | gaacatggt | 1080 |
| atcgcccatt | tccataatct | gctggcgcag | gtgtttaagg | actaatgaca | tcggcggcgg | 1140 |
| tattttccgc | cgctgggctg | attttttgatg | gagtacagca | atgtcagact | atcaaatgtt | 1200 |
| tgaagtacag | gtgagccagg | ttgaaccccct | taccgaacag | gtgaaacgct | tcacgctggt | 1260 |
| ggcaaccgat | ggcaaaccat | tacctgcgtt | taccggagga | agtcacgtca | ttgtgcagat | 1320 |
| gagcgatggt | gataaccagt | acagcaatgc | gtattcacta | ctgagttcgc | cgcatgacac | 1380 |
| ctcttgttat | cagattgccg | ttcggctgga | ggaaaactcg | cgcggcggtt | cccgctttt | 1440 |
| gcatcagcag | gtaaaagtgg | cgatcggtt | aacgatttca | acgcctaata | acctgtttgc | 1500 |
| gctaattccc | tcagccagaa | agcatctgtt | tatcgcgggc | ggtattggta | tcacccctt | 1560 |
| cctgtcgcac | atggcagagc | tgcaacacag | cgacgtcgac | tggcagctac | attactgctc | 1620 |
| gcgaaatcca | gaaagttgcg | catttcgtga | tgagctagtc | cagcatccgc | aggctgagaa | 1680 |
| agtccatttg | catcattcat | caaccggaac | acgactggaa | ttagcgcgat | tattggcgga | 1740 |
| tatcgaacct | ggcacacacg | tttatacctg | tggccccgag | cgctaattg | aagcggtaag | 1800 |
| aagtgaagct | gcgcgtctgg | acatcgccgc | cgatacgctg | cactttgagc | aatttgctat | 1860 |
| cgaagacaaa | accggcgatg | catttaccct | ggtgcttgcc | cgttccggaa | aagagtttgt | 1920 |
| ggtgccggaa | gagatgacta | ttttgcaggt | tattgaaaat | aataaagccg | cgaaagtgga | 1980 |

```
atgtttatgt cgtgaagggg tatgcggaac ctgcgaaaca gcaatactgg aaggtgaagc    2040
tgaccatcgg gatcaatatt ttagcgatga gagcgtgcc agccagcaaa gtatgttgat    2100
ctgttgttcg cgtgcgaagg gtaaacgcct ggtgttggat ttgtag                  2146
```

<210> SEQ ID NO 2
<211> LENGTH: 374
<212> TYPE: PRT
<213> ORGANISM: Escherichia coli

<400> SEQUENCE: 2

```
Met Ser Asn Leu Ser Pro Asp Phe Val Leu Pro Glu Asn Phe Cys Ala
1               5                   10                  15

Asn Pro Gln Glu Ala Trp Thr Ile Pro Ala Arg Phe Tyr Thr Asp Gln
            20                  25                  30

Asn Ala Phe Glu His Glu Lys Glu Asn Val Phe Ala Lys Ser Trp Ile
        35                  40                  45

Cys Val Ala His Ser Ser Glu Leu Ala Asn Ala Asn Asp Tyr Val Thr
    50                  55                  60

Arg Glu Ile Ile Gly Glu Ser Ile Val Leu Val Arg Gly Arg Asp Lys
65                  70                  75                  80

Val Leu Arg Ala Phe Tyr Asn Val Cys Pro His Arg Gly His Gln Leu
                85                  90                  95

Leu Ser Gly Glu Gly Lys Ala Lys Asn Val Ile Thr Cys Pro Tyr His
            100                 105                 110

Ala Trp Ala Phe Lys Leu Asp Gly Asn Leu Ala His Ala Arg Asn Cys
        115                 120                 125

Glu Asn Val Ala Asn Phe Asp Ser Asp Lys Ala Gln Leu Val Pro Val
    130                 135                 140

Arg Leu Glu Glu Tyr Ala Gly Phe Val Phe Ile Asn Met Asp Pro Asn
145                 150                 155                 160

Ala Thr Ser Val Glu Asp Gln Leu Pro Gly Leu Gly Ala Lys Val Leu
                165                 170                 175

Glu Ala Cys Pro Glu Val His Asp Leu Lys Leu Ala Ala Arg Phe Thr
            180                 185                 190

Thr Arg Thr Pro Ala Asn Trp Lys Asn Ile Val Asp Asn Tyr Leu Glu
        195                 200                 205

Cys Tyr His Cys Gly Pro Ala His Pro Gly Phe Ser Asp Ser Val Gln
    210                 215                 220

Val Asp Arg Tyr Trp His Thr Met His Gly Asn Trp Thr Leu Gln Tyr
225                 230                 235                 240

Gly Phe Ala Lys Pro Ser Glu Gln Ser Phe Lys Phe Glu Glu Gly Thr
                245                 250                 255

Asp Ala Ala Phe His Gly Phe Trp Leu Trp Pro Cys Thr Met Leu Asn
            260                 265                 270

Val Thr Pro Ile Lys Gly Met Met Thr Val Ile Tyr Glu Phe Pro Val
        275                 280                 285

Asp Ser Glu Thr Thr Leu Gln Asn Tyr Asp Ile Tyr Phe Thr Asn Glu
    290                 295                 300

Glu Leu Thr Asp Glu Gln Lys Ser Leu Ile Glu Trp Tyr Arg Asp Val
305                 310                 315                 320

Phe Arg Pro Glu Asp Leu Arg Leu Val Glu Ser Val Gln Lys Gly Leu
                325                 330                 335

Lys Ser Arg Gly Tyr Arg Gly Gln Gly Arg Ile Met Ala Asp Ser Ser
            340                 345                 350
```

Gly Ser Gly Ile Ser Glu His Gly Ile Ala His Phe His Asn Leu Leu
            355                 360                 365

Ala Gln Val Phe Lys Asp
    370

<210> SEQ ID NO 3
<211> LENGTH: 321
<212> TYPE: PRT
<213> ORGANISM: Escherichia coli

<400> SEQUENCE: 3

Met Ser Asp Tyr Gln Met Phe Glu Val Gln Val Ser Gln Val Glu Pro
1               5                   10                  15

Leu Thr Glu Gln Val Lys Arg Phe Thr Leu Val Ala Thr Asp Gly Lys
            20                  25                  30

Pro Leu Pro Ala Phe Thr Gly Gly Ser His Val Ile Val Gln Met Ser
        35                  40                  45

Asp Gly Asp Asn Gln Tyr Ser Asn Ala Tyr Ser Leu Leu Ser Ser Pro
    50                  55                  60

His Asp Thr Ser Cys Tyr Gln Ile Ala Val Arg Leu Glu Glu Asn Ser
65                  70                  75                  80

Arg Gly Gly Ser Arg Phe Leu His Gln Gln Val Lys Val Gly Asp Arg
                85                  90                  95

Leu Thr Ile Ser Thr Pro Asn Asn Leu Phe Ala Leu Ile Pro Ser Ala
            100                 105                 110

Arg Lys His Leu Phe Ile Ala Gly Gly Ile Gly Ile Thr Pro Phe Leu
        115                 120                 125

Ser His Met Ala Glu Leu Gln His Ser Asp Val Asp Trp Gln Leu His
    130                 135                 140

Tyr Cys Ser Arg Asn Pro Glu Ser Cys Ala Phe Arg Asp Glu Leu Val
145                 150                 155                 160

Gln His Pro Gln Ala Glu Lys Val His Leu His Ser Ser Thr Gly
                165                 170                 175

Thr Arg Leu Glu Leu Ala Arg Leu Leu Ala Asp Ile Glu Pro Gly Thr
            180                 185                 190

His Val Tyr Thr Cys Gly Pro Glu Ala Leu Ile Glu Ala Val Arg Ser
        195                 200                 205

Glu Ala Ala Arg Leu Asp Ile Ala Ala Asp Thr Leu His Phe Glu Gln
    210                 215                 220

Phe Ala Ile Glu Asp Lys Thr Gly Asp Ala Phe Thr Leu Val Leu Ala
225                 230                 235                 240

Arg Ser Gly Lys Glu Phe Val Val Pro Glu Glu Met Thr Ile Leu Gln
                245                 250                 255

Val Ile Glu Asn Asn Lys Ala Ala Lys Val Glu Cys Leu Cys Arg Glu
            260                 265                 270

Gly Val Cys Gly Thr Cys Glu Thr Ala Ile Leu Glu Gly Glu Ala Asp
        275                 280                 285

His Arg Asp Gln Tyr Phe Ser Asp Glu Glu Arg Ala Ser Gln Gln Ser
    290                 295                 300

Met Leu Ile Cys Cys Ser Arg Ala Lys Gly Lys Arg Leu Val Leu Asp
305                 310                 315                 320

Leu

<210> SEQ ID NO 4

```
<211> LENGTH: 33
<212> TYPE: DNA
<213> ORGANISM: Escherichia coli

<400> SEQUENCE: 4
catgccatat gagcaatctg agccctgact ttg                              33

<210> SEQ ID NO 5
<211> LENGTH: 38
<212> TYPE: DNA
<213> ORGANISM: Escherichia coli

<400> SEQUENCE: 5
catactgcag ctacaaatcc aacaccaggc gtttaccc                         38
```

METHODS FOR INHIBITING CONVERSION OF CARNITINE TO TRIMETHYLAMINE (TMA)

FIELD OF THE INVENTION

The invention generally relates to materials and methods for inhibiting trimethylamine production.

BACKGROUND

Trimethylamine (TMA) and its derivative trimethylamine-N-oxide (TMAO) are metabolites linked to disorders such as kidney disease, diabetes mellitus, trimethylaminuria, and cardiovascular disease (CVD). CVD is a general term encompassing a range of conditions affecting the heart and blood vessels, including atherosclerosis, coronary heart disease, cerebrovascular disease, heart failure, cardiomyopathy, atherothrombotic disease, aorto-iliac disease, and peripheral vascular disease. CVD is generally associated with conditions that involve narrowed, blocked, aneurysmal or dissection of one or more blood vessels, or thrombosis (blood clot formation). Complications associated with CVD include, but are not limited to, myocardial infarction, stroke, angina pectoris, acute coronary syndrome, transient ischemic attacks, congestive heart failure, aortic aneurysm, atrial fibrillation or flutter, ventricular arrhythmias, cardiac conduction abnormalities, need for revascularization and death. Revascularization can include but is not limited to angioplasty, stenting, coronary artery bypass grafting, repair or replacement of vascular shunt or access such as an arteriovenous fistula. Complications associated with atherothrombotic disease include, but are not limited to, myocardial infarction, stroke, pulmonary embolism, deep venous thrombosis. According to the World Health Organization, CVDs are the leading cause of death globally, with over 75% of deaths occurring in low- and middle-income countries. World Health Organization Fact Sheet No. 317, updated January 2015. The World Health Organization projects that diabetes will be the seventh leading cause of death in 2030. World Health Organization Fact Sheet No. 312, updated January 2015. Prevention and management of conditions associated with TMA and TMAO, including CVD and diabetes, is a major public health concern.

SUMMARY OF THE INVENTION

The disclosure is based, at least in part, on the discovery that compounds of Formula (I), Formula (II), Formula (III), and Formula (IV), inhibit carnitine metabolism by gut microbiota, resulting in reduction in the formation of trimethylamine (TMA) and trimethylamine N-oxide (TMAO). The disclosure provides compositions and methods for, e.g., inhibiting the conversion of carnitine to TMA in vitro and in vivo, for improving or maintaining cardiovascular, cerebrovascular and peripherovascular health, and for improving or preventing a condition associated with TMA and TMAO.

In certain aspects, the invention provides one or more methods of inhibiting the conversion of carnitine to trimethylamine (TMA) by a bacterium comprising: contacting the bacterium with a compound as set forth in Formula (I):

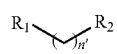

Formula (I)

wherein $R_1$ is selected from cyanate, isocyanate, thiocyanate, isothiocyanate, nitrile, isonitrile, or sulfhydryl; n' is selected from 0, 1, 2, 3, 4, 5, 6, 7, 8, 9, or 10; and $R_2$ is selected from alkyl, branched alkyl, heteroalkyl, cycloalkyl, heterocycloalkyl, aryl, or substituted carbonyl; wherein when $R_2$ is phenyl, $R_2$ is substituted with 0, 1, or 2 groups independently selected from alkyl, branched alkyl, heteroalkyl, cycloalkyl, heterocycloalkyl, halo, or aryl; with the condition that when $R_2$ is heteroalkyl or heterocycloalkyl, the heteroatom(s) are not S; and the condition that when n' is 2, $R_2$ is not unsubstituted phenyl.

In certain aspects, the invention provides one or more methods of inhibiting the conversion of carnitine to trimethylamine (TMA) in an individual. The method comprises administering to the individual one or more compounds as set forth in Formula (I):

Formula (I)

wherein $R_1$ is selected from cyanate, isocyanate, thiocyanate, isothiocyanate, nitrile, isonitrile, or sulfhydryl; n' is selected from 0, 1, 2, 3, 4, 5, 6, 7, 8, 9, or 10; and $R_2$ is selected from alkyl, branched alkyl, heteroalkyl, cycloalkyl, heterocycloalkyl, aryl, or substituted carbonyl; wherein when $R_2$ is phenyl, $R_2$ is substituted with 0, 1, or 2 groups independently selected from alkyl, branched alkyl, heteroalkyl, cycloalkyl, heterocycloalkyl, halo, or aryl; with the condition that when $R_2$ is heteroalkyl or heterocycloalkyl, the heteroatom(s) are not S; and the condition that when n' is 2, $R_2$ is not unsubstituted phenyl. The compound is administered in an amount effective to inhibit conversion of carnitine to TMA and TMAO in the individual.

In certain aspects, the invention provides one or more methods of improving a condition associated with the conversion of carnitine to trimethylamine by inhibiting the conversion of carnitine to trimethylamine (TMA) in an individual. The method comprises administering to the individual one or more compounds as set forth in Formula (I):

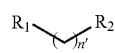

Formula (I)

wherein $R_1$ is selected from cyanate, isocyanate, thiocyanate, isothiocyanate, nitrile, isonitrile, or sulfhydryl; n' is selected from 0, 1, 2, 3, 4, 5, 6, 7, 8, 9, or 10; and $R_2$ is selected from alkyl, branched alkyl, heteroalkyl, cycloalkyl, heterocycloalkyl, aryl, or substituted carbonyl; wherein when $R_2$ is phenyl, $R_2$ is substituted with 0, 1, or 2 groups independently selected from alkyl, branched alkyl, heteroalkyl, cycloalkyl, heterocycloalkyl, halo, or aryl; with the condition that when $R_2$ is heteroalkyl or heterocycloalkyl, the heteroatom(s) are not S; and the condition that when n' is 2, $R_2$ is not unsubstituted phenyl. The compound is administered in an amount effective to treat or prevent the disease or condition associated with carnitine-related trimethylamine (TMA) in the individual.

The invention further provides one or more methods of improving or maintaining cardiovascular health. The method comprises administering to the individual one or more compounds as set forth in Formula (I) and described herein in an amount that improves or maintains cardiovascular health. The invention also provides one or more methods of improving a condition associated with the conversion of carnitine to trimethylamine (TMA) in an individual. The method comprises administering to the individual one or more compositions comprising a compound as set forth in Formula (I) and described herein in an amount effective to improve the condition. In some embodiments, the condition is trimethylaminuria, kidney disease, diabetes mellitus, or cardiovascular disease, e.g., angina, arrhythmia, atherosclerosis, cardiomyopathy, congestive heart failure, coronary artery disease (CAD), carotid artery disease, endocarditis, coronary thrombosis, myocardial infarction (MI), high blood pressure/hypertension, hypercholesterolemia/hyperlipidemia, atrial fibrillation or flutter, ventricular arrhythmias, cardiac conduction abnormalities, pulmonary embolism, deep venous thrombosis, peripheral artery disease (PAD), or stroke.

The invention further provides use of the compounds of Formula (I) for inhibiting the conversion of carnitine to TMA in vivo or in vitro, for improving or maintaining cardiovascular health, and for improving a condition associated with the conversion of carnitine to TMA. Also provided is the compound of Formula (I) for use in inhibiting the conversion of carnitine to TMA in vivo or in vitro, for improving or maintaining cardiovascular health, and for improving a condition associated with the conversion of carnitine to TMA.

The foregoing summary is not intended to define every aspect of the invention, and additional aspects are described in other sections, such as the Detailed Description. In addition, the invention includes, as an additional aspect, all embodiments of the invention narrower in scope in any way than the variations defined by specific paragraphs set forth herein. For example, certain aspects of the invention that are described as a genus, and it should be understood that every member of a genus is, individually, an aspect of the invention. Also, aspects described as a genus or selecting a member of a genus should be understood to embrace combinations of two or more members of the genus. With respect to aspects of the invention described or claimed with "a" or "an," it should be understood that these terms mean "one or more" unless context unambiguously requires a more restricted meaning. The term "or" should be understood to encompass items in the alternative or together, unless context unambiguously requires otherwise. If aspects of the invention are described as "comprising" a feature, embodiments also are contemplated "consisting of" or "consisting essentially of" the feature.

DETAILED DESCRIPTION OF THE INVENTION

Trimethylamine (TMA) synthesized by bacteria resident in the gut of mammals is oxidized in the liver to trimethylamine N-oxide (TMAO). Exemplary precursors to TMA include carnitine, acylcarnitines, gamma-butyrobetaine, crotonobetaine, dehydrocarnitine, and TMAO, many of which are derived from dietary sources such as, for example, dairy products and meats. Without wishing to be bound to a particular mechanism or biochemical pathway, the conversion of carnitine to TMA is mediated by an oxygenase/reductase, CntAB. Zhu et al., Proc. Natl. Acad. Sci. (2014), 111: 4268-4273. The reduction of carnitine conversion to TMA by bacteria in the gut of an individual leads to a reduction in TMA absorption from the gut, leading to a subsequent reduction in plasma TMAO following oxidation of TMA to TMAO by the Flavin Monooxygenase enzymes (i.e. FMO3) in the liver. Wang et al., Nature (2011), 472: 57-63. Lower plasma TMAO levels are related to a lower incidence of major cardiovascular events in humans. Tang et al., NEJM (2013) 368: 1575-1584. The conversion of carnitine to TMA in the gut of an individual may occur via a multi-step process, for example, by a two-step process via the metabolism of carnitine to gamma-butyrobetaine followed by the metabolism of gamma butyrobetaine to TMA, facilitated by at least two functionally different bacteria. Koeth et al., Cell Metabolism (2014), 20: 799-812. It will be appreciated that modulating the "conversion of carnitine to TMA" encompasses the conversion of carnitine-associated intermediates to TMA, including intermediates such as, but not limited to, gamma-butyrobetaine, crotonobetaine, dehydrocarnitine (Koeth et al.; Kleber (1997) FEMS Microbiolo. Lett. 147: 1-9), and TMAO.

All measurements referred to herein are made at about 22° C. to 25° C. (i.e. room temperature) unless otherwise specified.

As used herein the term "individual" includes both humans and other types of mammals sharing the TMAO pathway, such as domesticated animals, including but not limited to, domestic dogs (canines), cats (feline), horses, cows, ferrets, rabbits, pigs, rats, mice, gerbils, hamsters, horses, and the like.

A wide variety of individuals may wish to reduce the level of TMA produced by bacteria in their digestive tract. For example, individuals diagnosed with cardiovascular disease may be directed by a physician to take prescription drugs or effect lifestyle changes to modulate blood cholesterol levels to reduce the risk of serious cardiovascular events. Other individuals not previously diagnosed with cardiovascular disease but who wish to improve or maintain cardiovascular health may also wish to reduce plasma TMAO levels by reducing the level of TMA produced by digestive tract bacteria. As described further herein, a reduction in TMA (and, by extension, TMAO) is achieved by the compositions described herein, which include, for example, a dietary supplement or drug comprising isothiocyanates, such as the compounds of Formula (I), Formula (II), Formula (III), or Formula (IV).

As used herein, "dose" refers to a volume of medication, such as liquid medication or oral dosage unit, containing an amount of a drug active suitable for administration on a single occasion, according to sound medical practice. A dose can be orally administered. In one example, a dose can be a liquid medication and can be about 30 mL, in another example about 25 mL, in another example about 20 mL, in another example about 15 mL, and in another example about 10 mL. In another example, a dose of liquid medication can be from about 10 mL to about 75 mL, in another example from about 15 mL to about 50 mL, in another example from about 25 mL to about 40 mL, and in another example from about 28 mL to about 35 mL. In another example, the dose can be a solid dosage form and can be from about 5 g to about 25 mg, in another example from about 3 g to about 100 mg, in another example from about 2 g to about 250 mg, in another example from about 1.6 g to about 500 mg, and in another example from about 1 g to about 750 mg. In one example, the dose can be a solid dosage form wherein one dose is about 3 g and in another example one dose is about 1.6 g. The concentration of active ingredients can be adjusted to provide the proper doses of actives given the liquid dose size. In one example, the dose is intended to be administered every 4 hours, in another example every 6 hours, in another example every 8 hours, and in another example every 12 hours.

As used herein, "medication" refers to medications, such as pharmaceuticals, including prescription medications, over-the-counter medications, behind-the-counter medications and combinations thereof. In some examples, a medication can be a supplement which can contain vitamins, minerals, and botanicals (VMS).

Medication compositions can be in any suitable form including liquid compositions and solid oral dosage forms. Non limiting examples of liquid compositions can include syrups including cough syrups, respiratory preparations including MSR cold/flu medication, beverages, supplemental water, foam compositions, gel compositions, particles suspended in a liquid formulation, a solid in a gelatin or foam, saline wash and combinations thereof. Non-limiting examples of solid oral dosage forms can include tablets, capsules, caplets, sachets, sublingual dosage forms, buccal dosage forms, soft gels including Vicks® LiquiCaps™ and other liquid filled capsules, dissolvable dosage forms including dissolvable strips, films, gums including a center filled gum, gummies including a center filled gummy, lozenges, edible foods, such as food bars, center filled tablets, powder, granules, pellets, microspheres, nanospheres, beads, or nonpareils, and combinations thereof. Tablets can include compressed tablets, chewable tablets, dissolvable tablets, and the like. Tablets can include compressed tablets, chewable tablets, dissolvable tablets, and the like. In some examples, the medication can be applied to the skin, in an ointment such as Vicks® VapoRub®. In other examples, the medication can be inhaled, such as a nose spray or inhaler. In other examples, the medication can be in a drink, such as a warm beverage. In other examples, the medication can contain a pharmaceutical active. In other examples, the medication does not contain a pharmaceutical active and/or VMS but can alleviate symptoms and/or provide a health benefit at least in part, through the cooling sensation.

The medications can be in a form that is directly deliverable to the mouth, throat, and/or skin. In some example, the medication compositions can be delivered by a delivery device selected from droppers, pump, sprayers, liquid dropper, saline wash delivered via nasal passageway, cup, bottle, canister, pressurized sprayers, atomizers, air inhalation devices, squeezable sachets, power shots, blister cards, and other packaging and equipment, and combinations thereof. The sprayer, atomizer, and air inhalation devices can be associated with a battery or electric power source.

The disclosure provides, e.g., one or more methods of inhibiting the conversion of carnitine to trimethylamine (TMA), one or more methods of improving cardiovascular health, and one or more methods of improving a condition associated with conversion of carnitine to trimethylamine (TMA) comprising administering to the individual one or more compositions comprising a compound of Formula (I), Formula (II), Formula (III), or Formula (IV). Features of the compositions and methods are described below. Section headings are for convenience of reading and not intended to be limiting per se. The entire document is intended to be related as a unified disclosure, and it should be understood that all combinations of features described herein are contemplated, even if the combination of features are not found together in the same sentence, or paragraph, or section of this document. It will be understood that any feature of the methods or compounds described herein can be deleted, combined with, or substituted for, in whole or part, any other feature described herein.

Compounds

The method of the disclosure includes administering to the individual one or more compositions comprising a compound set forth in Formula (I):

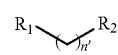

Formula (I)

wherein $R_1$ is selected from cyanate, isocyanate, thiocyanate, isothiocyanate, nitrile, isonitrile, or sulfhydryl; n' is selected from 0, 1, 2, 3, 4, 5, 6, 7, 8, 9, or 10; and $R_2$ is selected from alkyl, branched alkyl, heteroalkyl, cycloalkyl, heterocycloalkyl, aryl, or substituted carbonyl; wherein when $R_2$ is phenyl, $R_2$ is substituted with 0, 1, or 2 groups independently selected from alkyl, branched alkyl, heteroalkyl, cycloalkyl, heterocycloalkyl, halo, or aryl; with the condition that when $R_2$ is heteroalkyl or heterocycloalkyl, the heteroatom(s) are not S; and the condition that when n' is 2, $R_2$ is not unsubstituted phenyl. The compound is administered in an amount effective to achieve the desired effect, e.g., inhibit conversion of carnitine to TMA, improve or maintain cardiovascular health, and/or improve a condition associated with conversion of carnitine to TMA.

In some cases, $R_2$ is selected from methyl, ethyl, propyl (such as n-propyl or isopropyl), butyl (such as n-butyl, isobutyl, sec-butyl, or t-butyl), pentyl (e.g., 1-pentyl, 3-pentyl, 3-methylbutyl, 2-methylbutyl), hexyl (e.g., 1-hexyl), heptyl, octyl, nonyl, decyl, cyclopropyl, cyclobutyl, cyclopentyl, cyclohexyl, cycloheptyl, cyclooctyl, norbornyl, morpholino, piperidino, alkylamino (e.g., trialkylammonium, 3-(diethylamino)propyl, dimethylamino, diethylamino, (t-butoxycarbonyl)amino, ((t-butoxycarbonyl)amino)butyl), phenyl, substituted phenyl, naphthyl, arylcarbonyl (e.g., benzoyl), alkylcarbonyl, carboxy, alkoxycarbonyl, aminocarbonyl, alkylaminocarbonyl, benzhydryl, and alpha-methylbenzyl. In some cases, $R_2$ is phenyl substituted with 1 or 2 groups selected from methyl, ethyl, propyl, butyl, alkoxy (e.g., methoxy, ethoxy), alkylthio (e.g., methylthio, ethylthio), fluoro, bromo, chloro, iodo, (t-butoxycarbonyl)amino, or

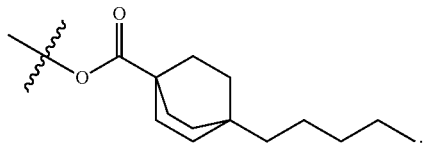 [SMILES: *OC(=O)C12CCC(CCCCC)(CC1)CC2]

In various embodiments, $R_1$ is an isothiocyanate. In some cases, the compound is selected from the group consisting of benzhydryl isothiocyanate, (S)-(+)-alpha-methylbenzyl isothiocyanate, and benzyl isothiocyanate. In various aspects of the invention, when $R_1$ is an isothiocyanate, n' is 0 (i.e., $CH_2$ is absent). In some cases, the compound is selected from the group consisting of cyclohexyl isothiocyanate, 4-bromophenyl isothiocyanate, 4-chlorophenyl isothiocyanate, phenyl isothiocyanate, 3-methoxyphenyl isothiocyanate, 4-methoxyphenyl isothiocyanate, 4-(methylthio) phenyl isothiocyanate, m-tolyl isothiocyanate, and 1-napthyl isothiocyanate.

In various embodiments when $R_1$ is an isothiocyanate, n' is at least 1 (e.g., n' is at least 1, at least 2, at least 3, at least 4, at least 5, at least 6, at least 7, at least 8, at least 9, or at least 10). An additional example of a compound of Formula (I) is 2-(4-chlorophenethyl) isothiocyanate.

Formula (I) also includes one or more salts or solvates of any compound encompassed by Formula (I).

In various embodiments, the method of the disclosure comprises administering to the individual one or more compositions comprising a compound of Formula (I) as set forth in Formula (II):

Formula (II)

wherein $R_2$ is as defined for Formula (I). The compound is administered in an amount effective to inhibit conversion of carnitine to TMA in the individual. In some cases, $R_2$ is selected from phenyl and substituted phenyl (e.g., phenyl substituted with 1 or 2 groups independently selected from methyl, ethyl, methoxy, methylthio, bromo, chloro, or (t-butoxycarbonyl)amino). In some cases the compound is selected from 4-methoxyphenyl isothiocyanate, phenyl isothiocyanate, 3-methoxyphenyl isothiocyanate, or 4-(methylthio)phenyl isothiocyanate.

Formula (II) also includes one or more salts or solvates of any compound encompassed by Formula (II).

In various embodiments, the methods of the disclosure comprise administering to the individual one or more compositions comprising a compound of Formula (I) as set forth in Formula (III):

Formula (III)

wherein n' and $R_2$ are as defined for Formula (I). The compound is administered in an amount effective to inhibit conversion of carnitine to TMA in the individual. In some cases, $R_2$ is haloaryl (e.g., halophenyl) and n' is 2. In some cases, the compound is 2-(4-chlorophenethyl) isothiocyanate.

Formula (III) also includes one or more salts or solvates of any compound encompassed by Formula (III).

In various aspects, the methods of the disclosure comprise administering to the individual one or more compositions comprising a compound of Formula (I) as set forth in Formula (IV):

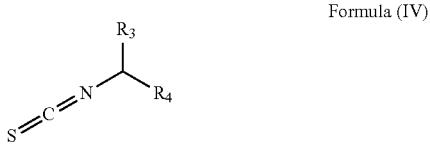

Formula (IV)

wherein $R_3$ is selected from hydrogen, alkyl, or aryl; and $R_4$ is aryl; wherein when $R_4$ is phenyl, $R_4$ is substituted with 0, 1, or 2 groups independently selected from alkyl, branched alkyl, heteroalkyl, cycloalkyl, heterocycloalkyl, halo, or aryl; with the condition that when $R_4$ is substituted with heteroalkyl or heterocycloalkyl, the heteroatom(s) are not S. The compound is administered in an amount effective to inhibit conversion of carnitine to TMA in the individual. In some cases, $R_3$ is selected from methyl, ethyl, propyl, butyl, pentyl, phenyl, or substituted phenyl, such as phenyl substituted with 1 or 2 groups selected from methyl, ethyl, propyl, butyl, alkoxy (e.g., methoxy, ethoxy), alkylthio (e.g., methylthio, ethylthio), fluoro, bromo, chloro, iodo, or (t-butoxycarbonyl)amino). In some cases, $R_4$ is selected from phenyl or substituted phenyl, such as phenyl substituted with 1 or 2 groups selected from methyl, ethyl, propyl, butyl, alkoxy (e.g., methoxy, ethoxy), alkylthio (e.g., methylthio, ethylthio), fluoro, bromo, chloro, iodo, or (t-butoxycarbonyl)amino.

Formula (IV) also includes one or more salts or solvates of any compound encompassed by Formula (IV).

"Alkyl" refers to straight chained and branched saturated hydrocarbon groups containing 1-30 carbon atoms (i.e., $C_1$-$C_{30}$), for example, 1-20 carbon atoms (i.e., $C_1$-$C_{20}$) or 1-10 carbon atoms (i.e., $C_1$-$C_{10}$). In various embodiments, the alkyl groups of $R_2$ and $R_3$ are independently selected from $C_1$-$C_7$ alkyls, i.e., alkyl groups having a number of carbon atoms encompassing the entire range (i.e., 1 to 7 carbon atoms), as well as all subgroups (e.g., 1-3, 1-6, 2-7, 1-5, 3-6, 5-7, 1, 2, 3, 4, 5, 6, and 7 carbon atoms). Nonlimiting examples of alkyl groups include methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group. Alkyl groups optionally can be substituted, for example, with one or more of hydroxy (OH), thiol (SH), aryl, heteroaryl, cycloalkyl, heterocyclyl, and amino. $R_2$ and/or $R_3$ may comprise a heteroalkyl so long as the heteroatom is not sulfur.

The term "heteroalkyl" is defined similarly as alkyl except the carbon chain contains one to three heteroatoms, such as heteroatoms independently selected from oxygen, nitrogen, or sulfur. Non-limiting examples of heteroalkyl include ethers, esters, ketones, primary amines, secondary amines, tertiary amines and quaternary amines, amides, sulfhydryls, alkyl sulfides, or carbamates. Unless otherwise indicated, a heteroalkyl group can be an unsubstituted heteroalkyl group or a substituted heteroalkyl group.

The term "cycloalkyl" refers to an aliphatic cyclic hydrocarbon group containing 3-8 carbon atoms (e.g., 3-5, 5-8, 3, 4, 5, 6, 7, or 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group.

The term "heterocycloalkyl" is defined similarly as cycloalkyl, except the ring contains one to three heteroatoms independently selected from oxygen, nitrogen, or sulfur. Nonlimiting examples of heterocycloalkyl groups include piperdine, tetrahydrofuran, tetrahydropyran, 4H-pyran, dihydrofuran, morpholine, thiophene, 1,4-dioxane, furan, pyrrole, pyrrolidine, imidazole, pyrazole, triazole, thiazole, pyrazine, pyran, oxazole, oxazine, thiazine, pyrimidine, piridazine, thiine, and the like. Cycloalkyl and heterocycloalkyl groups can be saturated or partially unsaturated ring systems optionally substituted with, for example, one to three groups, independently selected alkyl, alkyleneOH, $C(O)NH_2$, $NH_2$, oxo (=O), aryl, haloalkyl, halo, and OH. Heterocycloalkyl groups optionally can be further N-substituted with alkyl, hydroxyalkyl, alkylenearyl, and alkyleneheteroaryl.

The term "hydroxy" or "hydroxyl" refers to a "—OH" group. The term "amino" or "amine" refers to a —$NH_2$, or a —NH— group, wherein each hydrogen in each of Formula (I), Formula (II), Formula (III), or Formula (IV), can be replaced with an alkyl, cycloalkyl, aryl, heteroaryl, or heterocycloalkyl group. "Amine" includes cyclic amines optionally substituted with one or more additional heteroatoms. The term "carboxy" or "carboxyl" refers to a "—COOH" group. The term "thiol" or "sulfhydryl" refers to a "—SH" group. The term "cyano" refers to a —C≡N group, also designated —CN. The term "isocyanyl" refers to a —N≡C group. The term "isocyano" refers to a —N═C═O group. The term "isothiocyano" refers to a —N═C═S group. The term "nitro" refers to a —NO$_2$ group.

A "substituted" alkyl, alkenyl, alkynyl, cycloalkyl, cycloalkenyl, aryl, heteroaryl, or alkoxyl refers to an alkyl, alkenyl, alkynyl, cycloalkyl, cycloalkenyl, aryl, heteroaryl, or alkoxyl having at least one hydrogen radical that is substituted with a non-hydrogen radical (i.e., a substituent). Examples of non-hydrogen radicals (or substituents) include, but are not limited to, alkyl, cycloalkyl, alkenyl, cycloalkenyl, alkynyl, ether, aryl, heteroaryl, heterocycloalkyl, hydroxyl, oxy (or oxo), alkoxyl, ester, thioester, acyl, carboxyl, cyano, nitro, amino, amido, or sulfur. When a substituted alkyl group includes more than one non-hydrogen radical, the substituents can be bound to the same carbon or two or more different carbon atoms.

Salts or solvates, e.g., physiologically acceptable salts, of the disclosed compounds are contemplated and optionally are prepared by reacting the appropriate base or acid with a stoichiometric equivalent of the compound. Acids commonly employed to form physiologically acceptable salts include but are not limited to inorganic acids such as hydrogen bisulfide, hydrochloric acid, hydrobromic acid, hydroiodic acid, sulfuric acid and phosphoric acid, as well as organic mono- di- and tri-acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, malonic acid, para-bromophenylsulfonic acid, carbonic acid, succinic acid, glutaric acid, adipic acid, citric acid, benzoic acid and acetic acid, as well as related inorganic and organic acids. Physiologically acceptable salts include sulfate, pyrosulfate, bisulfate, sulfite, bisulfite, phosphate, monohydrogenphosphate, dihydrogenphosphate, metaphosphate, pyrophosphate, chloride, bromide, iodide, trifluoromethanesulfonate (or triflate), acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, O-hydroxybutyrate, glycolate, maleate, tartrate, methanesulfonate, propanesulfonate, naphthalene-1-sulfonate, naphthalene-2-sulfonate, mandelate and other salts. Physiologically acceptable acid addition salts include, e.g., those formed with mineral acids such as hydrochloric acid and hydrobromic acid and those formed with organic acids such as maleic acid.

Physiologically acceptable base addition salts may be formed with metals or amines, such as alkali and alkaline earth metals or organic amines. Physiologically acceptable salts of compounds may also be prepared with a physiologically acceptable cation. Suitable physiologically acceptable cations are well known in the art and include but are not limited to alkaline, alkaline earth, ammonium and quaternary ammonium cations. Carbonates or hydrogen carbonates are also options in this regard. Examples of metals used as cations are sodium, potassium, magnesium, ammonium, calcium, ferric, and the like. Examples of suitable amines include, but are not limited to, isopropylamine, histidine, N,N'-dibenzylethylenediamine, chloroprocaine, diethanolamine, dicyclohexylamine, ethylenediamine, N-methylglucamine, and procaine.

In some aspects of the invention, the compound is not naturally found in cruciferous vegetables (e.g., broccoli).

In various embodiments, the compound of Formula (I), Formula (II), Formula (III), or Formula (IV) demonstrates an IC$_{50}$ of $1\times10^{-3}$ or less, $5\times10^{-3}$ or less, $1\times10^{-4}$ or less, $5\times10^{-4}$ or less, $1\times10^{-5}$ or less, $5\times10^{-5}$ or less, or $1\times10^{-6}$ or less, or between $1\times10^{-6}$ and $1\times10^{-3}$, between $1\times10^{-6}$ and $1\times10^{-4}$, between $1\times10^{-6}$ and $1\times10^{-5}$, between $1\times10^{-5}$ and $1\times10^{-3}$, or between $1\times10^{-4}$ and $1\times10^{-3}$ (observed 50% inhibition of TMA (or TMAO) formation from carnitine; mol/L), optionally in the assay described in the Examples.

Methods

The invention includes one or more methods of inhibiting the conversion of carnitine to trimethylamine (TMA) in an individual comprising administering to the individual one or more compositions comprising a compound set forth in Formula (I), Formula (II), Formula (III), or Formula (IV), as described above under the subheading "Compounds." The individual of any of the embodiments described herein is a mammal, preferably a human, such as a human in need of reduced TMA levels, improvement of cardiovascular health, and the like. Optionally, the individual exhibits an elevated level of TMA or a metabolite thereof (e.g., TMAO, dimethylamine (DMA), or methylamine (MA, also known as monomethylamine or MMA)) prior to administration. In various embodiments, the individual suffers from cardiovascular disease, ingests a diet high in carnitine, or exhibits one or more CVD risk factors (e.g., smoking, stress, high total cholesterol, high LDL cholesterol, low HDL cholesterol, age, hypertension, family history of CVD, obesity, prediabetes, and/or diabetes).

One or more methods of inhibiting the conversion of carnitine to TMA in vitro also is contemplated. In this regard, the method comprises contacting a bacterium (e.g., a bacterium that is represented in the gut microbiota) or a bacterial lysate that metabolizes carnitine to produce TMA with a compound of Formula (I), Formula (II), Formula (III), or Formula (IV), as described above under the subheading "Compounds." In various embodiments, the bacterium is selected from *Proteus mirabilis, Proteus penneri, Clostridium ljungdahlii, C. scindens, C. aldenense, C. aminobutyricum, Collinsella tanakaei, Anaerococcus vaginalis, Eggerthella lenta, Edwardsiella tarda, Streptococcus dysgalactiae, Desultitobacterium hafniense, Klebsiella variicola, K. pneumonia, Escherichia coli, E. fergusonii*, or a combination thereof. The disclosure further provides one or more methods of identifying a compound that inhibits TMA production. A method comprises contacting a bacterium (e.g., a bacterium that is part of the gut microbiota) or a bacterial lysate that metabolizes carnitine to produce TMA with a candidate compound (e.g., a compound of Formula (I), Formula (II), Formula (III), or Formula (IV), as described above under the subheading "Compounds"), and detecting TMA (or a metabolite thereof). Optionally, the level of TMA (or metabolite thereof) produced by the bacterium in contact with the candidate compound is compared to (a) the level of TMA produced by a bacterium or lysate not contacted with a candidate compound or known TMA inhibitor or (b) the level of TMA produced by the bacterium prior to contact with the candidate compound. A reduction in the level of TMA produced by the bacterium indicates that the candidate compound inhibits conversion of carnitine to TMA.

One or more methods of inhibiting the conversion of carnitine to TMA in vitro is also contemplated, wherein in certain embodiments a method comprises contacting bacteria or bacterial lysate with a compound of Formula (I), Formula (II), Formula (III), or Formula (IV). In various embodiments, the bacteria comprises a single bacterial species or strain, or contains a mixture of two or more (e.g., three, four, five, or more) different bacterial species or bacterial strains. Similarly, the bacterial lysate is generated from a single bacteria species or strain or multiple different bacterial species or strains.

It will be appreciated that "inhibiting conversion of carnitine to TMA" does not require complete elimination of TMA production via carnitine metabolism. Any reduction in TMA formation from carnitine or a carnitine related metabolite as a precursor is contemplated, e.g., at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% reduction; or from about 1% to about 100%, about 10% to about 90%, about 20% to about 80%, about 30% to about 70%, about 40% to about 60%; or any other numerical range which is narrower and which falls within such broader numerical range, as if such narrower numerical ranges were all expressly written herein.

Any suitable method for measuring TMA in vitro or in vivo can be used in the context of the invention. TMA, metabolites of TMA (e.g., TMAO, DMA, or MA), stable isotopes of TMA (e.g., deuterium labeled TMA, such as d3-, d6-, or d9-TMA), stable isotopes of TMAO (e.g., deuterium labeled TMAO, such as d3-, d6-, or d9-TMAO), stable isotopes of DMA (e.g., deuterium labeled DMA, such as d3- or d6-DMA), stable isotopes of MA (e.g., deuterium labeled MA, such as d3-MA), and/or carnitine (including stable isotopes of carnitine, for example d9-carnitine) can be assessed quantitatively or qualitatively. Exemplary methods of detecting and quantifying TMA are described in, e.g., U.S. Pub. No. 2010/00285517, the disclosure of which is incorporated herein by reference in its entirety. For example, levels of TMA (or trimethylamine-N-oxide (TMAO), DMA, or MA) and/or carnitine are optionally measured via mass spectrometry, ultraviolet spectroscopy, or nuclear magnetic resonance spectroscopy. Mass spectrometers include an ionizing source (e.g., electrospray ionization), an analyzer to separate the ions formed in the ionization source according to their mass-to-charge (m/z) ratios, and a detector for the charged ions. In tandem mass spectrometry, two or more analyzers are included. Such methods are standard in the art and include, for example, HPLC with on-line electrospray ionization (ESI) and tandem mass spectrometry.

In various embodiments, TMA and/or TMAO is measured in a biological sample from an individual. Biological samples include, but are not limited to, whole blood, plasma, serum, urine, feces, saliva, sweat, and/or tissue. The sample may be collected using any clinically-acceptable practice and, if desired, diluted in an appropriate buffer solution, heparinized, concentrated, or fractionated. Any of a number of aqueous buffer solutions at physiological pH, such as phosphate, Tris, or the like, can be used. Acidified buffers also may be used. For example, the final pH after adding buffer to sample is optionally between pH 1 and pH 6, e.g., between pH 1.5 and pH 3.0.

Optionally, levels of TMA (or a metabolite or stable isotope thereof) and/or carnitine in the biological sample is compared to a control value. The control value utilized will depend on the embodiment of the invention. In one aspect, the control value is the level of TMA and/or TMAO produced in the individual (or by the bacterium) prior to administration or exposure to the compound of Formula (I), Formula (II), Formula (III), or Formula (IV). Alternatively, the control value is based on levels measured in comparable samples obtained from a reference cohort (e.g., the general population, individuals diagnosed with a CVD or other TMA-associated condition, individuals not previously diagnosed with a TMA-associated condition, nonsmokers, and the like). Levels of TMA and/or TMAO and/or carnitine may be compared to a single control value or to a range of control values. An individual is optionally identified as having an enhanced or elevated level of TMA prior to administration by comparing the amount of TMA in a biological sample from the individual with a control value.

The invention further provides one or more methods of improving cardiovascular health of an individual. In certain embodiments a method comprises administering to the individual one or more compositions comprising a compound set forth in Formula (I), Formula (II), Formula (III), or Formula (IV), as described above under the subheading "Compounds" in an amount effective to improve cardiovascular health. Cardiovascular health is assessed by testing arterial elasticity, blood pressure, ankle/brachial index, electrocardiogram, ventricular ultrasound, platelet function (i.e. platelet aggregation), and blood/urine tests to measure, e.g., cholesterol, albumin excretion, C-reactive protein, or plasma B-type peptide (BNP) concentration. In various aspects of the invention, administration of the compound of Formula (I), Formula (II), Formula (III), or Formula (IV), improves or maintains one or more of the assay outcomes within normal ranges. Normal ranges of outcomes of each test are known in the art. Improvement in cardiovascular health is, in some embodiments, marked by a reduction in circulating total cholesterol levels, reduction in circulating low density lipoproteins (LDLs), reduction in circulating triglycerides, and/or reduction in blood pressure.

The invention also includes one or more methods of improving a condition associated with conversion of carnitine to trimethylamine (TMA) in an individual in need thereof. In certain embodiments a method comprises administering to the individual one or more compositions comprising a compound of Formula (I), Formula II, Formula (III), or Formula (IV), as described above under the subheading "Compounds" in an amount effective to improve the condition. "Improving a condition" refers to any reduction in the severity and/or onset of symptoms associated with a disorder caused, at least in part, by TMA. One of ordinary skill in the art will appreciate that any degree of protection from, or amelioration of, a TMA-related disorder or symptom associated therewith is beneficial to an individual, such as a human. The quality of life of an individual is improved by reducing to any degree the severity of symptoms in an individual and/or delaying the appearance of symptoms. Accordingly, the method in one aspect is performed as soon as possible after it has been determined that an individual is at risk for developing a TMA-related disorder or as soon as possible after a TMA-related disorder is detected.

The condition associated with the conversion of carnitine to trimethylamine is, in various aspects of the invention, a cardiovascular disease, reduced or impaired kidney function, chronic kidney disease, end stage renal disease, trimethylaminuria, or diabetes mellitus. The term "cardiovascular disease" (CVD) is used in the art in reference to conditions affecting the heart, heart valves, and vasculature (e.g., arteries and veins) of the body and encompasses diseases and conditions including, but not limited to, arteriosclerosis, atherosclerosis, myocardial infarction, acute coronary syndrome, angina, congestive heart failure, aortic aneurysm, aortic dissection, iliac or femoral aneurysm, pulmonary embolism, primary hypertension, atrial fibrillation, stroke, transient ischemic attack, systolic dysfunction, diastolic dysfunction, myocarditis, atrial tachycardia, ventricular fibrillation, endocarditis, arteriopathy, vasculitis, atherosclerotic plaque, vulnerable plaque, acute coronary syndrome, acute ischemic attack, sudden cardiac death, peripheral vascular disease, coronary artery disease (CAD), peripheral artery disease (PAD), and cerebrovascular disease.

In one aspect, the condition is atherosclerosis. Atherosclerosis involves the formation of atheromatous plaques that lead to narrowing ("stenosis') of the vasculature, which can ultimately lead to partial or complete occlusion or rupture (aneurism) of the vessel, heart failure, aortic dissection, and ischemic events such as myocardial infarction and stroke. In various non-limiting embodiments, the inventive method inhibits, reduces, or reverses (in whole or in part) the onset or progression of atherosclerosis (e.g., reducing or preventing hardening or thickening of the arteries, plaque formation, endothelium damage, and/or arterial inflammation).

In various embodiments, administration of the compound of Formula (I), Formula (II) or Formula (III), or Formula (IV), results in reduced TMA and/or TMAO levels, reduced total cholesterol levels, reduced LDL levels, increased HDL levels, reduced triglyceride levels, and/or normalized levels of other biomarkers associated with CVD (e.g., excreted albumin, C-reactive protein, or plasma B-type peptide (BNP)). In some embodiments, the compound of Formula (I), Formula (II), Formula (III), or Formula (IV), reduces the risk of cardiovascular disease, reduced or impaired kidney function, chronic kidney disease, end stage renal disease, trimethylaminuria, or diabetes mellitus when administered to an individual.

Administration Regimens and Compositions

The amount of compound administered to the individual is sufficient to inhibit (in whole or in part) formation of TMA from carnitine. In various aspects of the disclosure, the amount improves cardiovascular health and/or achieves a beneficial biological response with respect to an unwanted condition associated with TMA (e.g., the amount is sufficient to ameliorate, slow the progression, or prevent a condition (e.g., CVD)). The effect can be detected by, for example, an improvement in clinical condition, reduction in symptoms, or by any of the assays or clinical diagnostic tests described herein. The precise effective amount for an individual can depend upon the individual's body weight, size, and health; the nature and extent of the condition; and the compound or combination of agents selected for administration. In various aspects, the amount of compound administered to the individual is about 0.001 mg/kg to about 1000 mg/kg. Specific ranges of doses in mg/kg include about 0.1 mg/kg to about 500 mg/kg, about 0.5 mg/kg to about 200 mg/kg, about 1 mg/kg to about 100 mg/kg, about 2 mg/kg to about 50 mg/kg, and about 5 mg/kg to about 30 mg/kg. An effective amount may be administered to the individual as a single deployment of compound or as a divided doses (i.e., a single dose administered in multiple subunits contemporaneously or close in time). An amount of compound is optionally delivered one, two, or three times a day; one, two, or three times a week; or one, two, three, or four times a month. The compound may be delivered as a prodrug which is converted to an active drug in vitro or in vivo.

The compound or composition comprising the compound is administered by any route that allows inhibition of carnitine conversion to TMA. The compound or composition comprising the compound is, in various aspects of the invention, delivered to an individual parenterally (e.g., intravenously, intraperitoneally, intrapulmonary, subcutaneously or intramuscularly), intrathecally, topically, transdermally, rectally, orally, sublingually, nasally or by inhalation. In various preferred embodiments, the compound is administered to the gastrointestinal tract via, e.g., ingestion. Sustained release formulations may also be employed to achieve a controlled release of the compound when in contact with body fluids in the gastrointestinal tract. Sustained release formulations are known in the art, and typically include a polymer matrix of a biological degradable polymer, a water-soluble polymer, or a mixture of both, optionally with suitable surfactants.

The invention provides one or more compositions comprising the compound of Formula (I), Formula (II), Formula (III), or Formula (IV), formulated with one or more physiologically acceptable excipients, carriers, stabilizers, or diluent for use in the methods described herein. Excipients include, but are not limited to, carrier molecules that include large, slowly metabolized macromolecules such as proteins, polysaccharides, polylactic acids, polyglycolic acids, polymeric amino acids, amino acid copolymers, antioxidants (e.g., ascorbic acid), chelating agents (e.g., EDTA), carbohydrates (e.g., dextrin, hydroxyalkylcellulose, and/or hydroxyalkylmethylcellulose), liposomes, stearic acid, liquids (e.g., oils, water, saline, glycerol and/or ethanol), wetting or emulsifying agents, pH buffering substances, and the like.

Formulations for, e.g., parenteral or oral administration, are typically solids (for example, a lyophilized powder or cake), liquid solutions, emulsions or suspensions, while inhalable formulations for pulmonary administration are generally liquids or powders. Exemplary dosage forms include, but are not limited to, tablets, troches, lozenges, aqueous or oil suspensions, non-aqueous solutions, powders, dispersible powders or granules (including micronized particles or nanoparticles), emulsions, hard or soft capsules, hard or soft liquid-filled capsules, gelatin capsules, syrups, and elixirs. Solid dose formulations, for example tablets or liquid filled capsules may be uncoated or may be coated by known techniques including microencapsulation to delay disintegration and adsorption in the gastrointestinal tract. Solid dose formulations may be coated to target delivery to a specific region of the digestive tract. For example, the formulation may be enteric coated to target delivery of the formulation to the small intestine, the large intestine, or to the colon. Additional exemplary dosage forms may comprise coated microcapsules or coated microbeads in a suspension or liquid chassis. In some embodiments, the compound of Formula (I), Formula (II), Formula (III), or Formula (IV) is provided as a dietary (e.g., food or drink) supplement. Dietary supplements are orally dosed and typically comprise vitamins, minerals, herbs or other botanicals, amino acids, enzymes, organ tissues, tissues from glands, or metabolites. In one example, the compound of Formula (I), Formula (II), Formula (III), or Formula (IV), is provided as a food in the form of a bar.

In some embodiments, the compounds described herein are formulated for oral administration in a lipid-based formulation suitable for low solubility compounds. Lipid-based formulations can generally enhance the oral bioavailability of such compounds. As such, the composition comprises in some aspects, an amount of a compound described herein together with at least one excipient selected from medium chain fatty acids and propylene glycol esters thereof (e.g., propylene glycol esters of edible fatty acids, such as caprylic and capric fatty acids) and physiologically acceptable surfactants, such as polyoxyl 40 hydrogenated castor oil.

In some embodiments, the compound described herein is provided in a delayed release formulation and/or is released in a specific region of the digestive tract of an individual. For example, the formulation may be provided such that the compound is released from an orally dosed formulation in the distal portion of the digestive tract such as the ileum or the colon. In certain embodiments, the delayed release formulation may release the compounds at a specific pH, or at a range of pH for the targeted delivery within the digestive tract of an individual. The compound may be released for example, between pH 6.0 and pH 9.0, between pH 6.5 and pH 8.0, between pH 6.5 and pH 7.5, between pH 7.0 and pH 7.5, or between pH 7.0 and pH 8.0.

In certain embodiments a method of the invention optionally comprises administering a second agent to the individual. The term "second agent" merely serves to distinguish the agent from the compound of Formula (I), Formula (II), Formula (III), or Formula (IV), and is not meant to limit the number of additional agents used in a method or denote an order of administration. One or more second agents are optionally incorporated in the composition with the compound of Formula (I), Formula (II), Formula III, or Formula (IV), administered concurrently but in separate dosage forms, or administered separately in time.

Exemplary second agents include, but are not limited to, antimicrobials (such as antibiotics that kill bacteria in the gut), agents that improve intestinal motility (such as fiber or psyllium), agents that further reduce TMA levels in the gut including sequestering agents (such as activated charcoal or copper chlorophyllin), and/or agents that further reduce the production of TMA metabolites, and agents that improve one or more aspects of cardiovascular health, such as agents that normalize blood pressure, decrease vascular inflammation, reduce platelet activation, normalize lipid abnormalities. In various embodiments, the second agent is selected from the group consisting of Omega 3 oil, salicylic acid (aspirin), dimethylbutanol, garlic oil, olive oil, krill oil, Co enzyme Q-10, a probiotic, a prebiotic, a dietary fiber, psyllium husk, bismuth salts, phytosterols, grape seed oil, green tea extract, vitamin D, an antioxidant (such as vitamin C and vitamin E), turmeric, curcumin, resveratrol, activated charcoal, or copper chlorophyllin. Optionally, the composition comprises dimethylbutanol and/or inhibitors of the formation of TMA from precursors other than carnitine (e.g., choline).

Alternatively or in addition, the methods of the disclosure may further comprise administration of one or more cardiovascular disease therapies. Examples of therapies include, but are not limited to, statins (e.g., Lipitor™ (atorvastatin), Pravachol™ (pravastatin), Zocor™ (simvastatin), Mevacor™ (lovastatin), and Lescol™ (fluvastatin)) or other agents that interfere with the activity of HMGCoA reductase, nicotinic acid (niacin, which lowers LDL cholesterol levels), fibrates (which lower blood triglyceride levels and include, e.g., Bezafibrate (e.g. Bezalip®), Ciprofibrate (e.g. Modalim®), Clofibrate, Gemfibrozil (e.g. Lopid®) and Fenofibrate (e.g. TriCor®)), bile acid resins (e.g., Cholestyramine, Colestipol (Colestid), and Cholsevelam (Welchol)), cholesterol absorption inhibitors (e.g., Ezetimibe (Zetia®, Ezetrol®, Ezemibe®)), phytosterols (e.g., sitosterol (Take Control (Lipton)), sitostanol (Benechol), or stigmastanol), alginates and pectins, lecithin, and nutraceuticals (e.g., extract of green tea and other extracts that include polyphenols, particularly epigallocatechin gallate (EGCG), Cholest-Arrest™ (500 mg garlic and 200 mg lecithin). Cholestaway™ (700 mg Calcium carbonate, 170 mg magnesium oxidem 50 µg chromium picolinate), Cholest-Off™ (900 mg of plant sterols/stanols), Guggul Bolic (750 mg gugulipid (*Commiphora mukul* gum resin), and Kyolic® (600 mg aged garlic extract and 380 mg lecithin)).

In related variations of the preceding embodiments, one or more compositions comprising a compound of Formula (I), Formula (II), Formula III, or Formula (IV), described herein, alone or in combination with one or more second agents(s), are optionally arranged in a kit or package or unit dose, such as a kit or package or unit dose permitting co-administration of multiple agents. In another aspect, the composition comprising a compound of Formula (I), Formula (II), Formula III, or Formula (IV), and the one or more second agents are in admixture. In various embodiments, the component(s) of the kit or package or unit dose are packaged with instructions for administering the component(s) to an individual.

Other aspects and advantages of the present invention will be understood upon consideration of the following illustrative examples, which are not intended to be limiting in any way.

EXAMPLE

This example provides an exemplary assay for identifying and characterizing compounds that inhibit the formation of TMA from carnitine.

*Escherichia coli* BL21*DE3::pET30a-Ec yeaWX #1 (Ec YeaWX) strain was generated as described below. The contiguous *Escherichia coli* coding sequence yeaW (equivalent to uniprot ID P0ABR7.1 (YeaW) (SEQ ID NO: 2)) and yeaX (equivalent to uniprot ID P76254.1 (YeaX) (SEQ ID NO: 3)) were PCR amplified from *Escherichia coli* strain K-12 substr. BW25113 genomic DNA. PCR primers (YeaW_Nde_I_fwd2—SEQ ID NO: 4; YeaX_rev2—SEQ ID NO: 5) were designed to create a 5' NdeI restriction site including the ATG start codon of yeaW and create a PstI restriction site just 3' of the yeaX TAG stop codon.

The amplicon was restricted and cloned into the NdeI and PstI sites of the plasmid pET30a downstream of the inducible T7 promoter. A blast search of the resulting cloned amplicon DNA sequence (SEQ ID NO: 1) corresponded to nucleotide range 1884665 to 1886810 of *Escherichia coli* str. K-12 substr. MG1655 (NCBI Accession # NC_000913). The construct was transformed and grown in *E. coli* BL21 (DE3) and the recombinant yeaWX overexpressed by addition of isopropyl β-D-1-thiogalactopyranoside (IPTG).

| SEQ ID NO | Sequence |
| --- | --- |
| 1 | *Escherichia coli* yeaWX amplicon sequence |
| 2 | uniprot ID P0ABR7.1, YeaW |
| 3 | uniprot ID P76254.1, YeaX |
| 4 | YeaW_Nde I_fwd2 |
| 5 | YeaX_rev2 |

A sequence listing that sets forth the nucleotide sequences for SEQ ID NO: 1 to 5 herein is being filed concurrently with the present application as an ASCII text file titled "14120&M_Nucleotide_Sequence_Listing_ST25." The ASCII text file was created on 28 Nov. 2016 and is 10 Kbytes in size. In accordance with MPEP § 605.08 and 37 CFR § 1.52(e), the subject matter in the ASCII text file is incorporated herein by reference.

The bacteria were grown aerobically in 50 mL LB broth (Difco #244620; 10 g/L Tryptone, 5 g/L yeast extract, 10 g/L NaCl, 50 µg/mL kanamycin), in a 500 mL Erlenmeyer flask. The cultures were inoculated from glycerol stock of BL21*DE3::pET30a-Ec yeaWX #1 strain. Strains were cultured all day at 37° C. with 250 rpm shaking. Two 300 mL Minimal M9 Medium (6 g/L $Na_2HPO_4$, 3 g/L $KH_2PO_4$, 0.5 g/L NaCl, 1 g/L $NH_4Cl$, 0.1 mM $CaCl_2$, 1 mM $MgSO_4$, 0.2% Dextrose, 1 mg/L Thiamine, 50 µg/mL kanamycin), in 1 L Erlenmeyer flasks, were inoculated with 5 mL of the LB broth day culture and cultured overnight at 37° C. with 250 rpm shaking. The overnight cultures were used to inoculate twelve 1 L cultures of Minimal M9 media in 2.8 L fluted Erlenmeyer flasks to an OD 600 nm of 0.05 (typically approximately 28 mLs), which were grown at 37° C. with 250 rpm shaking until an $OD_{600}$ of approximately 0.4 was reached. Expression of YeaWX was induced with 1 mM IPTG and the induced cultures were further grown overnight at 37° C. with 250 rpm shaking. The biomass was pelleted by centrifugation at 6000×g for 12 minutes at 4° C. The cell pellet was suspended in 240 mL of ice-cold 1× Phosphate Buffered Saline ($Ca^{2+}$ and $Mg^{2+}$ free). Ninety micrograms of Lysozyme (Sigma # L6876 Lot # SLBG8654V; Sigma-Aldrich Corp., St. Louis, Mo.) was added and incubated with 320 rpm shaking for 30 minutes at 4° C. Lysis was achieved via French press with a 4° C. prechilled 1" diameter chamber at 1000 psi (high ratio; internal PSI equivalent ~16000). The lysate was centrifuged at 6,000×g for 12 minutes at 4° C. to pellet extra debris. Glycerol was added to the centrifuged lysate supernatant at a final concentration of 15% A protein concentration of the centrifuged lysate supernatant was determined by a BCA Protein Assay Kit (Pierce #23225), typically in the 2.5 to 4.5 mg/ml range. The centrifuged Ec YeaWX lysate supernatant was aliquoted into 20 mL volumes and stored frozen at −80° C.

Ec YeaWX lysate was diluted to 2.0 mg/mL protein with 1× Dulbecco's phosphate buffered saline (DPBS) plus 15% glycerol. Nicotinamide adenine dinucleotide phosphate (NADPH) was added to 250 µM. One hundred and fifty microliters of Ec YeaWX lysate was dispensed into a deep-well plate (polypropylene, 2 mL volume, Corning Axygen catalogue # P-DW-20-C). Candidate $IC_{50}$ compounds from TABLE 1 (below) and vehicle control (respective vehicle control of DMSO or water), or control compounds ($IC_{50}$ control, 8-Quinolinol hemisulfate salt (Sigma Catalog #55100)) were added at a1:100 dilution (e.g., 1.5 µL per well). The plates were agitated on a plate shaker for 1 minute. d9-carnitine chloride (1.5 µL of 5 mM) was added to all wells to reach a final d9-carnitine chloride concentration of 50 µM.

The plates were again agitated on a plate shaker for 1 minute and incubated at 37° C. for two hours. After incubation, 1.5 µL of formic acid was added to each well (final concentration=1% formic acid). The plates were agitated on a plate shaker for 1 minute and placed on ice. Cell lysate samples were spiked with stable isotope labeled internal standard (22.5 µL of 6 µg/mL of 13C3-trimethylamine (13C3-TMA) was added to each sample), then d9-trimethylamine (d9-TMA), trimethylamine (TMA) and 13C3-TMA were isolated from the lysate after protein precipitation as described below. Acetonitrile acidified with 0.1% formic acid, 600 µL, was added to each sample which was then centrifuged (2,100 g for 20 minutes) to pellet the protein and other precipitates. The supernatant was removed and analyzed as described below. The TMA, d9-TMA and 13C3-TMA in the isolated supernatant samples were subjected to gradient High Performance Liquid Chromatography HPLC analysis on a Waters Atlantis HILIC Silica column, from Waters Corp., Milford, Mass., (2.1×50 mm, 3 µm particles) with an Atlantis Silica HILIC Sentry guard column, from Waters Corp., Milford, Mass., (100 Å, 3 µm, 2.1 mm×10 mm), 10 mM ammonium formate in water with 0.1% formic acid as mobile phase A and 0.1% formic acid in acetonitrile as mobile phase B. Detection and quantitation was achieved by tandem mass spectrometry operating under multiple reaction monitoring (MRM) MS/MS conditions (m/z 60.1→44.1 for TMA, m/z 69.1→49.1 for d9-TMA, m/z 63.0→46.1 for 13C3-TMA). TMA and d9-TMA calibration standards (STD), prepared in 80/20/0.1% acetonitrile/Water/Formic Acid, were used to construct a regression curve by plotting the response (peak area TMA/peak area 13C3-TMA) versus concentration for each standard. The concentrations of TMA and d9-TMA in the cell lysate were determined by interpolation from the quadratic (1/×2) regression curve.

$IC_{50}$ measurements of representative compounds of Formula (I) are set forth in TABLE 1.

TABLE 1

| # | Compound | TMA Inhibition ($IC_{50}$, mol/L) | SMILES | |
|---|---|---|---|---|
| 1 | 2-Methoxy-5-methylphenyl isothiocyanate | 6.16E−05 | CC1=CC=C(OC)C(N=C=S)=C1 | 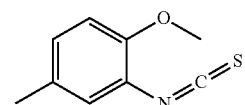 |
| 2 | tert-Butyl isothiocyanate | >0.001 | CC(C)(N=C=S)C | 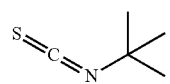 |
| 3 | m-Tolyl isothiocyanate | 1.45E−05 | CC1=CC(N=C=S)=CC=C1 | 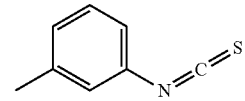 |

TABLE 1-continued

| # | Compound | TMA Inhibition (IC$_{50}$, mol/L) | SMILES |
|---|---|---|---|
| 4 | 4-(Methylthio)phenyl isothiocyanate | 1.08E−05 | CSC1=CC=C(N=C=S)C=C1 |
| 5 | Benzyl isothiocyanate | 8.37E−06 | S=C=NCC1=CC=CC=C1 |
| 6 | 1-pentyl isothiocyanate | 3.22E−05 | CCCCCN=C=S |
| 7 | 3-(Diethylamino)propyl isothiocyanate | 0.0001458 | CCN(CCCN=C=S)CC |
| 8 | Cyclohexylmethyl isothiocyanate | 3.81E−05 | S=C=NCC1CCCCC1 |
| 9 | 2-(4-Chlorophenethyl) isothiocyanate | 1.27E−05 | ClC1=CC=C(C=C1)CCN=C=S |
| 10 | sec-butyl isothiocyanate | 0.0001463 | CCC(C)N=C=S |
| 11 | Ethyl isothiocyanate | 8.22E−05 | CCN=C=S |
| 12 | Isobutyl isothiocyanate | 7.45E−05 | CC(CN=C=S)C |
| 13 | Butyl isothiocyanate | 6.36E−05 | CCCCN=C=S |
| 14 | Methyl isothiocyanate | 0.0001492 | CN=C=S |
| 15 | Isopropyl isothiocyanate | 0.0001996 | CC(C)N=C=S |
| 16 | 1-isothiocyanato-3-methylbutane | 7.59E−05 | CC(CCN=C=S)C |
| 17 | Hexyl isothiocyanate | 4.35E−05 | CCCCCCN=C=S |

TABLE 1-continued

| # | Compound | TMA Inhibition (IC$_{50}$, mol/L) | SMILES | |
|---|---|---|---|---|
| 18 | Phenyl isothiocyanate | 6.45E−06 | S=C=NC1=CC=CC=C1 | |
| 19 | 1-Naphthyl isothiocyanate | 1.25E−05 | S=C=NC1=C2C=CC=CC2=CC=C1 | |
| 20 | 4-Bromophenyl isothiocyanate | 4.72E−06 | BrC1=CC=C(C=C1)N=C=S | |
| 21 | Benzoyl isothiocyanate | 0.0001379 | O=C(C1=CC=CC=C1)N=C=S | |
| 22 | N-Boc-4-isothiocyanatobutylamine | 1.77E−05 | S=C=NCCCCNC(OC(C)(C)C)=O | |
| 23 | N-Boc-4-isothiocyanatoaniline | 1.57E−05 | S=C=NC1=CC=C(NC(OC(C)(C)C)=O)C=C1 | |
| 24 | 3-(4-Morpholino)propyl isothiocyanate | 6.85E−05 | S=C=NCCCN1CCOCC1 | |
| 25 | 2-(4-Morpholino)ethyl isothiocyanate | 6.90E−05 | S=C=NCCN1CCOCC1 | |
| 26 | (S)-(+)-alpha-Methylbenzyl isothiocyanate | 7.34E−06 | C[C@@H](C1=CC=CC=C1)N=C=S | |
| 27 | 4-Chlorophenyl isothiocyanate | 4.57E−06 | ClC1=CC=C(N=C=S)C=C1 | |
| 28 | 4-Methoxyphenyl isothiocyanate | 5.76E−06 | COC1=CC=C(N=C=S)C=C1 | |

TABLE 1-continued

| # | Compound | TMA Inhibition (IC$_{50}$, mol/L) | SMILES | |
|---|---|---|---|---|
| 29 | exo-2-Norbornyl-isothiocyanate | 2.16E−05 | S=C=NC1CC2CCC1C2 | |
| 30 | Cyclohexyl isothiocyanate | 3.88E−05 | S=C=NC1CCCCC1 | |
| 31 | 4-Ethylphenyl isothiocyanate | 1.73E−05 | CCC1=CC=C(N=C=S)C=C1 | |
| 32 | 2-Methoxyphenyl isothiocyanate | 3.33E−05 | COC1=CC=CC=C1N=C=S | |
| 33 | 2,5-Dimethoxyphenyl isothiocyanate | 4.77E−05 | COC1=CC=C(OC)C(N=C=S)=C1 | |
| 34 | 3-Methoxyphenyl isothiocyanate | 9.59E−06 | COC1=CC(N=C=S)=CC=C1 | |
| 35 | 2-Piperidinoethyl isothiocyanate | 0.0001043 | S=C=NCCN1CCCCC1 | |
| 36 | Ethyl isothiocyanatoacetate | 2.999E−05 | O=C(OCC)CN=C=S | |
| 37 | 4-Isothiocyanatophenyl 4-pentylbicyclo[2.2.2]octane-1-carboxylate | >0.001 | O=C(C1(CC2)CCC2(CCCCC)CC1)OC3=CC=C(N=C=S)C=C3 | |

TABLE 1-continued

| # | Compound | TMA Inhibition (IC$_{50}$, mol/L) | SMILES |
|---|---|---|---|
| 38 | Benzhydryl isothiocyanate | 3.05E−06 | S=C=NC(C1=CC=CC=C1)C2=CC=CC=C2 |
| 39 | 2,3,4-Tri-O-acetyl-α-D-arabinopyranosyl isothiocyanate | 5.012E−05 | CC(OC1C(N=C=S)OCC(OC(C)=O)C1OC(C)=O)=O |
| 40 | Ethanamine, N,N-diethyl-2-isothiocyanato | 3.199E−04 | CCN(CCN=C=S)CC |
| 41 | 3-isothiocyanato-N,N-dimethyl-1-Propanamine | 3.199E−04 | CN(C)CCCN=C=S |
| 42 | 2-Isothiocyanato-N,N-dimethylethanamine | 1.637E−04 | CN(CCN=C=S)C |
| 43 | Pentane, 3-isocyanato- | 1.648E−04 | CCC(N=C=S)CC |
| 44 | Butane, 1-isocyanato-2-methyl- | 5.309E−05 | CC(CN=C=S)CC |
| 45 | 2-Isocyanato-N,N,N-trimethylethanaminium iodide | 1.154E−04 | C[N+](CCN=C=S)(C)C.[I−] |

The Example provides exemplary methods of identifying and quantitating TMA in a sample, as well as screening candidate inhibitory compounds. All compounds in TABLE 1 were found to inhibit the conversion of carnitine to TMA. The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of inhibiting the conversion of carnitine to trimethylamine (TMA) by a bacterium in an individual in need thereof, comprising: providing to an individual about 0.001 mg/kg to about 1000 mg/kg of a compound set forth in Formula (I):

Formula (I)

wherein $R_1$ is sec-butyl isothiocyanate or ethyl isothiocyanate;
n' is selected from 0, 1, 2, 3, 4, 5, 6, 7, 8, 9, or 10; and
$R_2$ is selected from alkyl, heteroalkyl, aryl, or substituted carbonyl;
wherein when $R_2$ is heteroalkyl the heteroatom(s) are not S; and
including any acceptable salts or solvates thereof;
inhibiting the conversion of carnitine-associated intermediates to TMA, wherein the intermediates are at least one of gamma-butyrobetaine, crotonobetaine, or dehydrocarnitine, wherein the bacterium is at least one selected from the group consisting of *Proteus mirabilis, Proteus penneri, Clostridium ljungdahlii, C. scindens, C. aldenense, C. aminobutyricum, Collinsella tanakaei, Anaerococcus vaginalis, Eggerthella lenta, Edwardsiella tarda, Streptococcus dysgalactiae, Desultitobacterium hafniense, Klebsiella variicola, K. pneumonia, Escherichia coli* or *E. fergusonii*.

2. The method of claim 1, wherein n' is 0.

3. The method of claim 1, wherein n' is at least 1.

4. The method of claim 1 further comprising contacting the bacterium with a second agent that is at least one of Omega 3 oil, salicylic acid, dimethylbutanol, garlic oil, olive oil, krill oil, Co enzyme Q-10, a probiotic, a prebiotic, dietary fiber, psyllium husk, bismuth salts, phytosterols, grape seed oil, green tea extract, vitamin D, an antioxidant, turmeric, curcumin, resveratrol, activated charcoal, or copper chlorophyllin.

5. The method of claim 1, wherein conversion of carnitine to trimethylamine (TMA) is inhibited by from about 1% to about 100%.

6. The method of claim 1, wherein the compound has a formula as set forth in Formula (II):

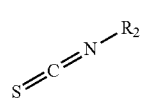

Formula (II)

wherein $R_2$ is as defined for Formula (I); and
including any acceptable salts or solvates thereof.

7. The method of claim 1, wherein the compound has a formula as set forth in Formula (III):

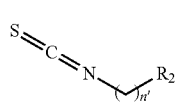

Formula (III)

wherein n' and $R_2$ are as defined for Formula (I); and
including any acceptable salts or solvates thereof.

* * * * *